(12) United States Patent
Katakura (10) Patent No.: US 8,582,217 B2
(45) Date of Patent: Nov. 12, 2013

(54) OPTICAL SYSTEM FOR ENDOSCOPE

(71) Applicant: Olympus Medical Systems Corp., Tokyo (JP)

(72) Inventor: Masahiro Katakura, Tokyo (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/793,690

(22) Filed: Mar. 11, 2013

(65) Prior Publication Data

US 2013/0215523 A1 Aug. 22, 2013

Related U.S. Application Data

(63) Continuation of application No. PCT/JP2012/072926, filed on Sep. 7, 2012.

(30) Foreign Application Priority Data

Oct. 6, 2011 (JP) ................. 2011-221667

(51) Int. Cl.
*G02B 13/04* (2006.01)
*G02B 9/00* (2006.01)

(52) U.S. Cl.
USPC ............................ 359/753; 359/749; 359/754

(58) Field of Classification Search
USPC ......................... 359/749–753, 754
See application file for complete search history.

(56) References Cited

U.S. PATENT DOCUMENTS 5,424,877 A * 6/1995 Tsuyuki et al. ............... 359/663
2012/0007972 A1 * 1/2012 Uzawa ........................ 348/65

FOREIGN PATENT DOCUMENTS

| EP | 2 402 808 | 1/2012 |
|----|-----------|--------|
| JP | 2005-227426 | 8/2005 |
| JP | 2007-279632 | 10/2007 |
| JP | 2008-058387 | 3/2008 |
| JP | 2009-276371 | 11/2009 |
| JP | 4819203 | 9/2011 |
| JP | 5006476 | 6/2012 |
| WO | 2011/070897 | 6/2011 |
| WO | 2011/148822 | 12/2011 |

OTHER PUBLICATIONS

International Search Report, issued in corresponding International Application No. PCT/JP2012/072926.

* cited by examiner

*Primary Examiner* — Scott J Sugarman
(74) *Attorney, Agent, or Firm* — Kenyon & Kenyon LLP (57) ABSTRACT

An optical system for an endoscope includes a negative lens-group, an aperture diaphragm and a positive lens-group in this order from an object side, wherein the negative lens-group includes a negative first-lens and a negative second-lens in this order from the object side; and wherein the optical system meets conditional expressions (1) and (2):

$$0.05 < H(100) \times (nd01-1)/Rf01 < 0.38 \quad (1)$$

and $$0.5 < enp/FL < 2.5 \quad (2),$$

where: H(100) is a height at which a principal ray with a field angle of incidence of 100 degrees falls on a surface on the object side of the first lens; Rf01 is a curvature radius of the surface on the object side of the first-lens; nd01 is a refractive index of the first-lens; FL is a focal length of an entire system; and enp is a distance between an entrance pupil and the surface on the object side of the first lens.

8 Claims, 12 Drawing Sheets

OPTICAL SYSTEM FOR ENDOSCOPE

CROSS REFERENCE TO RELATED APPLICATION

This application is a continuation application of PCT/JP2012/072926 filed on Sep. 7, 2012 and claims benefit of Japanese Application No. 2011-221667 filed in Japan on Oct. 6, 2011, the entire contents of which are incorporated herein by this reference.

BACKGROUND OF THE INVENTION

1. Field of the Invention

The present invention relates to an optical system for an endoscope that has a field angle of no less than 200 degrees.

2. Description of the Related Art

Since endoscopes are intended to, for example, observe an inside of a body cavity, optical systems for endoscopes are demanded to have a small size and a wide angle, and in particular, optical systems for urological endoscopes need to be small in a radial direction.

As examples of optical systems having a field angle of no less than 200 degrees, which can be employed in endoscopes, those described in Japanese Patent Application Laid-Open Publication No. 2007-279632 (Patent Literature 1), Japanese Patent Application Laid-Open Publication No. 2008-058387 (Patent Literature 2), Japanese Patent Application Laid-Open Publication No. 2005-227426 (Patent Literature 3) and Japanese Patent Application Laid-Open Publication No. 2009-276371 (Patent Literature 4) are known.

Among them, the optical systems disclosed in Patent Literatures 1 to 3 each include a negative first lens, a negative second lens, a positive third lens, an aperture diaphragm and a positive lens group in this order from the object side and have a field angle of 200 degrees.

Also, the optical system disclosed in Patent Literature 4 includes a negative first lens, a negative second lens, a filter, an aperture diaphragm and a positive lens group in this order from the object side and has a field angle of 200 degrees.

SUMMARY OF THE INVENTION

An optical system for an endoscope according to an aspect of the present invention includes a negative lens group, an aperture diaphragm and a positive lens group in this order from an object side, wherein the negative lens group includes a negative first lens and a negative second lens in this order from the object side; and wherein the optical system meets conditional expressions (1) and (2):

$$0.05 < H(100) \times (nd01-1)/Rf01 < 0.38 \quad (1)$$

and $$0.5 < enp/FL < 2.5 \quad (2),$$

where: $H(100)$ is a height at which a principal ray with a field angle of incidence of 100 degrees falls on a surface on the object side of the first lens; $Rf01$ is a curvature radius of the surface on the object side of the first lens; $nd01$ is a refractive index of the first lens; $FL$ is a focal length of an entire system; and $enp$ is a distance between an entrance pupil and the surface on the object side of the first lens.

DETAILED DESCRIPTION OF THE PREFERRED EMBODIMENT

An embodiment of the present invention will be described below with reference to the drawings.

Embodiment

An optical system for an endoscope according to the present embodiment includes a negative lens group, an aperture diaphragm and a positive lens group in this order from the object side. Furthermore, the negative lens group includes a negative first lens and a negative second lens in this order from the object side. Consequently, a position of an entrance pupil moves to the object side, enabling reduction in diameter of the negative first lens. In addition, the number of lenses in the respective groups included in the optical system for an endoscope can be reduced, enabling reduction in total length and costs.

Here, the optical system for an endoscope meets conditional expressions (1) and (2):

$$0.05 < H(100) \times (nd01-1)/Rf01 < 0.38 \quad (1);$$

and $$0.5 < enp/FL < 2.5 \quad (2),$$

where H(100) is a height at which a principal ray with a field angle of incidence of 100 degrees falls on a surface on the object side of the first lens, Rf01 is a curvature radius of the surface on the object side of the first lens, nd01 is a refractive index of the first lens, FL is a focal length of an entire system, and enp is a distance between the entrance pupil and the surface on the object side of the first lens.

First, conditional expression (1) is a conditional expression relating to the height at which a principal ray with a field angle of incidence of 100 degrees falls on the surface on the object side of the first lens, and the refractive index and a curvature of the first lens. Conditional expression (1) is a part of Abbe's invariant and is a mathematical expression that defines an amount of change in angle of a light ray before and after refraction at the first surface, that is, an amount of refraction. If $H(100) \times (nd01-1)/Rf01$ exceeds the upper limit in conditional expression (1), the amount of refraction is excessively large, unfavorably resulting in easy occurrence of an off-axis aberration. Also, if $H(100) \times (nd01-1)/Rf01$ falls below the lower limit in conditional expression (1), the amount of refraction is excessively small, unfavorably resulting in an increase in diameter of the lens.

Next, conditional expression (2) is a conditional expression relating to the entrance pupil. As long as enp/FL falls within the range in conditional expression (2), a proper entrance pupil position is achieved, enabling a decrease in size without occurrence of various aberrations in a large amount. On the other hand, if enp/FL exceeds the upper limit in conditional expression (2), the lens is unfavorably enlarged in the radial direction. Also, if enp/FL falls below the lower limit in conditional expression (2), it is necessary to significantly increase powers of the negative first lens and the negative second lens, unfavorably resulting in easy occurrence of various aberrations in a large amount.

Note that conditional expressions (1) and (2), which have been described above, are preferably:

$$0.1 < H(100) \times (nd01-1)/Rf01 < 0.37 \quad (1)';$$

and $$1.0 < enp/FL < 2.0 \quad (2)',$$

and more preferably:

$$0.15 < H(100) \times (nd01-1)/Rf01 < 0.36 \quad (1)'';$$

and $$1.4 < enp/FL < 1.6 \quad (2)''.$$

The optical system for an endoscope may further meet conditional expressions (3) and (4):

$$0.5 < H(100)/FL < 3.5 \quad (3);$$

and $$1.1 < (r1+r2)/(r1-r2) < 1.9 \quad (4),$$

where r1 is the curvature radius of the surface on the object side of the first lens and r2 is a curvature radius of a surface on the image side of the first lens.

Conditional expression (3) is a conditional expression relating to the height at which a principal ray with a field angle of incidence of 100 degrees falls on the surface on the object side of the first lens. If H(100)/FL falls below the lower limit in conditional expression (3), the lens is extremely excessively small in the radial direction, causing the need to increase the power of the negative first lens, unfavorably resulting in occurrence of axial and off-axis aberrations. Also, if H(100)/FL exceeds the upper limit in conditional expression (3), the lens is unfavorably enlarged in the radial direction.

Conditional expression (4) is a conditional expression relating to a shape factor of the first lens in the negative lens group. As long as (r1+r2)/(r1-r2) falls within the range in conditional expression (4), a necessary negative power can be provided while a wide field angle is provided. If (r1+r2)/(r1-r2) falls below the lower limit in conditional expression (4), the refractive power of the negative first lens is unfavorably lowered. Also, if (r1+r2)/(r1-r2) exceeds the upper limit in conditional expression (4), the productivity of the lens is unfavorably lowered substantially.

Note that conditional expressions (3) and (4), which have been described above, are preferably:

$$1.0 < H(100)/FL < 2.0 \quad (3)';$$

and $$1.2 < (r1+r2)/(r1-r2) < 1.8 \quad (4)',$$

and more preferably:

$$1.8 < H(100)/FL < 2.1 \quad (3)'';$$

and $$1.3 < (r1+r2)/(r1-r2) < 1.7 \quad (4)''.$$

Where a lens system incident angle $\omega = 100$, the optical system for an endoscope may further meet conditional expression (5):

$$0.00 < |EX(\omega)|/\omega < 0.03 \quad (5),$$

where $EX(\omega)$ is an angle at which a principal ray incident at the incident angle $\omega$ exits from the optical system.

Conditional expression (5) is an expression relating to an exit angle relative to an incident angle in the optical system, and represents a telecentricity (image-side telecentricity) of the optical system for an incident angle of 100 degrees. If the telecentricity is lost, effects such as a decrease in brightness in the periphery and/or color mixture occur due to the oblique incidence property of image pickup devices such as CCD and C-MOS. Conditional expression (5) is a conditional expression for preventing such deterioration in image quality.

The optical system for an endoscope may further meet conditional expression (6):

$$-8.0 < F\_front/F\_rear < -0.1 \quad (6),$$

where F_front is a focal length of the negative lens group and F_rear is a focal length of the positive lens group.

Conditional expression (6) is a conditional expression relating to power allocation for the negative lens group and the positive lens group. If F_front/F_rear falls within the range in conditional expression (6), the positive power can be favorably shared, enabling a chromatic aberration, a spherical aberration and a coma aberration to be favorably corrected. On the other hand, if F_front/F_rear exceeds the upper limit or falls below the lower limit in conditional expression (6), either of the lens groups have an excessively large power, unfavorably resulting in easy occurrence of various aberrations.

Note that conditional expression (6), which has been described above, is preferably:

$$-6.0 < F\_front/F\_rear < -1.0 \quad (6)',$$

and more preferably:

$$-4.0 < F\_front/F\_rear < -3.0 \quad (6)''.$$

The optical system for an endoscope may further meet conditional expressions (7) and (8):

$$1.77 < nd1 < 2.42 \quad (7);$$

and $$1.9 < nd2 < 2.42 \quad (8),$$

where nd1 is the refractive index of the negative first lens and nd2 is a refractive index of the negative second lens.

Conditional expression (7) is a conditional expression relating to the refractive index of the negative first lens and conditional expression (8) is a conditional expression relating to the refractive index of the negative second lens. As long as nd1 falls within the range in conditional expression (7) and nd2 falls within the range in conditional expression (8), the refractive indices are both are adequate, enabling provision of a proper negative power without an extreme increase in curvatures on the object side of the negative first lens and the negative second lens. On the other hand, if nd1 falls below the lower limit in conditional expression (7) or nd2 falls below the lower limit in conditional expression (8), the negative first lens or the negative second lens needs to have an extremely large curvature, unfavorably resulting in easy occurrence of an off-axis aberration. Also, if nd1 exceeds the upper limit in conditional expression (7) or nd2 exceeds the upper limit in conditional expression (8), unfavorably, procurement of the lenses themselves (or procurement of glass material) becomes significantly difficult and high costs are needed.

Furthermore, the positive lens group in the optical system for an endoscope may include at least one positive lens, and a joined lens including a positive lens and a negative lens, in this order from the object side.

The optical system for an endoscope may further meet conditional expression (9):

$$0.1 < PW\_1/PW\_2 < 0.26 \quad (9),$$

where PW_1 is the power of the negative first lens and PW_2 is the power of the negative second lens.

Conditional expression (9) is a conditional expression relating to power allocation in the negative lens group. As long as PW_1/PW_2 falls within the range in conditional expression (9), proper power allocation is achieved, enabling the lens diameter to be kept small while a wide field angle is maintained. On the other hand, if PW_1/PW_2 exceeds the upper limit in conditional expression (9), the power of the first lens becomes excessively large, unfavorably resulting in failure to maintain a wide field angle as well as easy occurrence of, in particular, an off-axis aberration. Also, if PW_1/PW_2 falls below the lower limit in conditional expression (9), the power of the second lens becomes too large, unfavorably resulting in easy occurrence of an off-axis aberration, and also unfavorably resulting in enlargement of the first lens.

Note that conditional expression (9), which has been described above, is preferably:

$$0.12 < PW\_1/PW\_2 < 0.255 \quad (9)',$$

and more preferably:

$$0.15 < PW\_1/PW\_2 < 0.25 \quad (9)''.$$

All of optical elements having a power in the optical system for an endoscope may be spherical lenses.

Use of non-spherical lenses or diffractive optical elements as the optical elements having a power results in an increase in costs. Accordingly, the optical elements having a power (optical elements except, e.g., the aperture diaphragm and an optical filter) in the optical system for an endoscope are all provided by spherical lenses, enabling the costs to be suppressed to be low.

Next, first to sixth examples of the optical system for an endoscope according to the present embodiment will be described with reference to Table 1 and FIGS. 1A to 6B.

Table 1 is a table indicating values obtained according to the above-described conditional expressions for an optical system for an endoscope according to each of the first to sixth examples. As can be seen from the table, all of the optical systems for an endoscope according to the first to sixth examples meet conditional expressions (1) to (9) (further meet respective conditional expressions (1)', (1)'', (2)', (2)'', (3)', (3)'', (4)', (4)'', (6)', (6)'', (9)' and (9)'').

TABLE 1

|  | ex1 | ex2 | ex3 | ex4 | ex5 | ex6 |
| --- | --- | --- | --- | --- | --- | --- |
| H(100) × (nd01 − 1)/Rf01 | 0.150 | 0.195 | 0.308 | 0.247 | 0.356 | 0.343 |
| enp/FL | 1.453 | 1.469 | 1.503 | 1.492 | 1.476 | 1.515 |
| H(100)/FL | 1.951 | 1.994 | 2.097 | 2.046 | 1.874 | 1.911 |
| (r1 + r2)/(r1 − r2) | 1.355 | 1.423 | 1.552 | 1.495 | 1.621 | 1.663 |
| \|EX(ω)\|/ω | 0.0018 | 0.0020 | 0.0022 | 0.0026 | 0.0004 | 0.0003 |
| F_front/F_rear | −3.116 | −3.224 | −3.509 | −3.298 | −3.686 | −3.894 |
| nd1 | 1.770 | 1.883 | 2.170 | 2.002 | 2.420 | 2.420 |
| nd2 | 2.003 | 2.003 | 2.003 | 2.003 | 2.003 | 2.420 |
| PW_1/PW_2 | 0.151 | 0.175 | 0.216 | 0.198 | 0.237 | 0.249 |

Configurations of the optical systems for an endoscope according to the first to sixth examples along respective optical paths are illustrated in FIGS. 1A, 2A, 3A, 4A, 5A and 6A, respectively. Also, diagrams of aberrations in the optical systems for an endoscope according to the first to sixth examples are illustrated in FIGS. 1B, 2B, 3B, 4B, 5B and 6B, respectively.

Here, in the diagrams of the configurations of the optical systems for an endoscope along the respective optical paths, symbol L1 denotes a first lens, symbol L2 denotes a second lens, symbol S denotes an aperture diaphragm, symbol L3 denotes a third lens, symbol L4 denotes a fourth lens, symbol OF denotes an optical member contemplated to be an optical filter such as a laser cut filter, an infrared cut filter or an optical low-pass filter, symbol L5 denotes a fifth lens, symbol L6 denotes a sixth lens, symbol L7 denotes a seventh lens, symbol CG denotes an image pickup device cover glass, symbol AL denotes an adhesion layer, and symbol SG denotes an image pickup device chip sealing glass, respectively.

Furthermore, in optical surfaces in the first to sixth examples, r1 is an object side of the first lens L1, r2 is an image side of the first lens L1, r3 is an object side of the second lens L2, r4 is an image side of the second lens L2, r5 is the aperture diaphragm S, r6 is an object side of the third lens L3, r7 is an image side of the third lens L3, r8 is an object side of the fourth lens L4, r9 is an image side of the fourth lens L4, r10 is an object side of the optical member OF, r11 is an image side of the optical member OF, r12 is an object side of the fifth lens L5, r13 is a surface of joining between the fifth lens L5 and the sixth lens L6, r14 is a surface of joining between the sixth lens L6 and the seventh lens L7, r15 is an image side of the seventh lens L7, r16 is an object side of the image pickup device cover glass CG, r17 is an image side of the image pickup device cover glass CG (object side of the adhesion layer AL), r18 is an object side of the image pickup device chip sealing glass SG (image side of the adhesion layer AL), and r19 is an image surface IM, which is an image side of the image pickup device chip sealing glass SG, and the numbers provided to the respective optical surfaces are surface numbers of the respective optical surfaces. Likewise, the numbers provided to the surface distances d in FIGS. 1A to 6A are the surface numbers of surfaces on the object side of the respective surface distances d.

The optical systems for an endoscope according to the first to sixth examples of the present embodiment each include a first lens group G1, which is a negative lens group, the aperture diaphragm S, and a second lens group G2, which is a positive lens group, in this order from the object side. Furthermore, the first lens group G1, which is a negative lens group, includes the first lens L1, which is a negative meniscus lens with a convex surface directed to the object side, and the second lens L2, which is a negative lens, in this order from the object side. Here, the second lens L2 is a biconcave lens in the first to fourth examples, and a negative meniscus lens with a convex surface directed to the object side in the fifth and sixth examples.

Also, the second lens group G2, which is a positive lens group, includes the third lens L3, which is a positive meniscus lens with a convex surface directed to the image side, the fourth lens L4, which is a plano-convex lens (positive lens) with a convex surface directed to the image side, the fifth lens L5, which is a biconvex lens (positive lens), the sixth lens L6, which is a biconcave lens (negative lens) and the seventh lens L7, which is a biconvex lens (positive lens), in this order from the object side, and the optical member OF is disposed between the fourth lens L4 and the fifth lens L5.

Here, the fifth lens L5 and the sixth lens L6 are joined to each other via the optical surface r13, and also, the sixth lens L6 and the seventh lens L7 are joined to each other via the optical surface r14, and as a result, the three lenses, i.e., the fifth to seventh lenses L5 to L7 form a joined lens. Consequently, the second lens group G2, which is a positive lens group, can be regarded as including at least one positive lens, and a joined lens including a positive lens and a negative lens.

All of the first to seventh lenses L1 to L7 are spherical lenses.

First Example

Figure 1A:
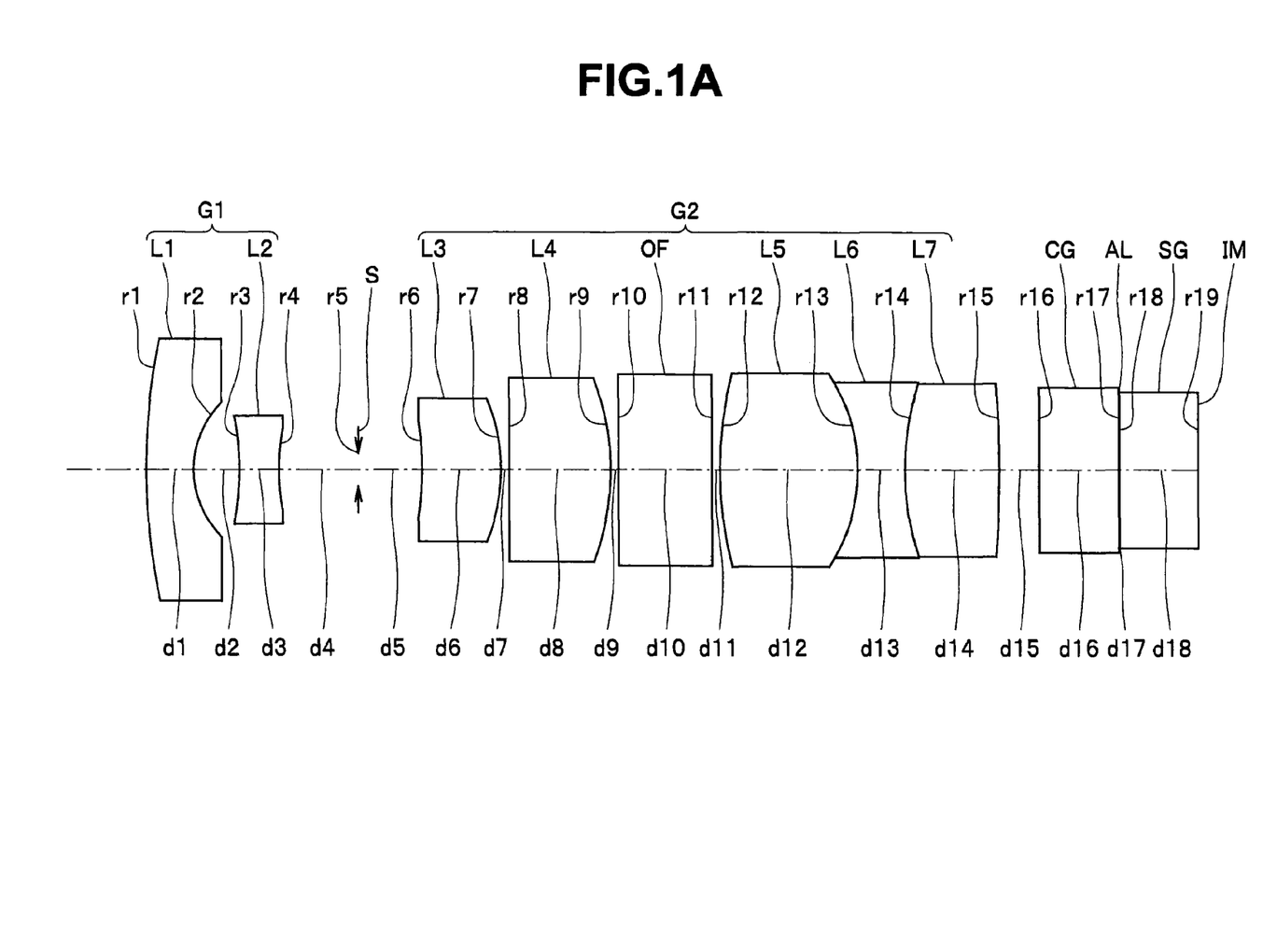
FIG. 1A is a diagram illustrating a configuration of an optical system for an endoscope according to a first example of an embodiment of the present invention, along an optical path.
Figure 1B:
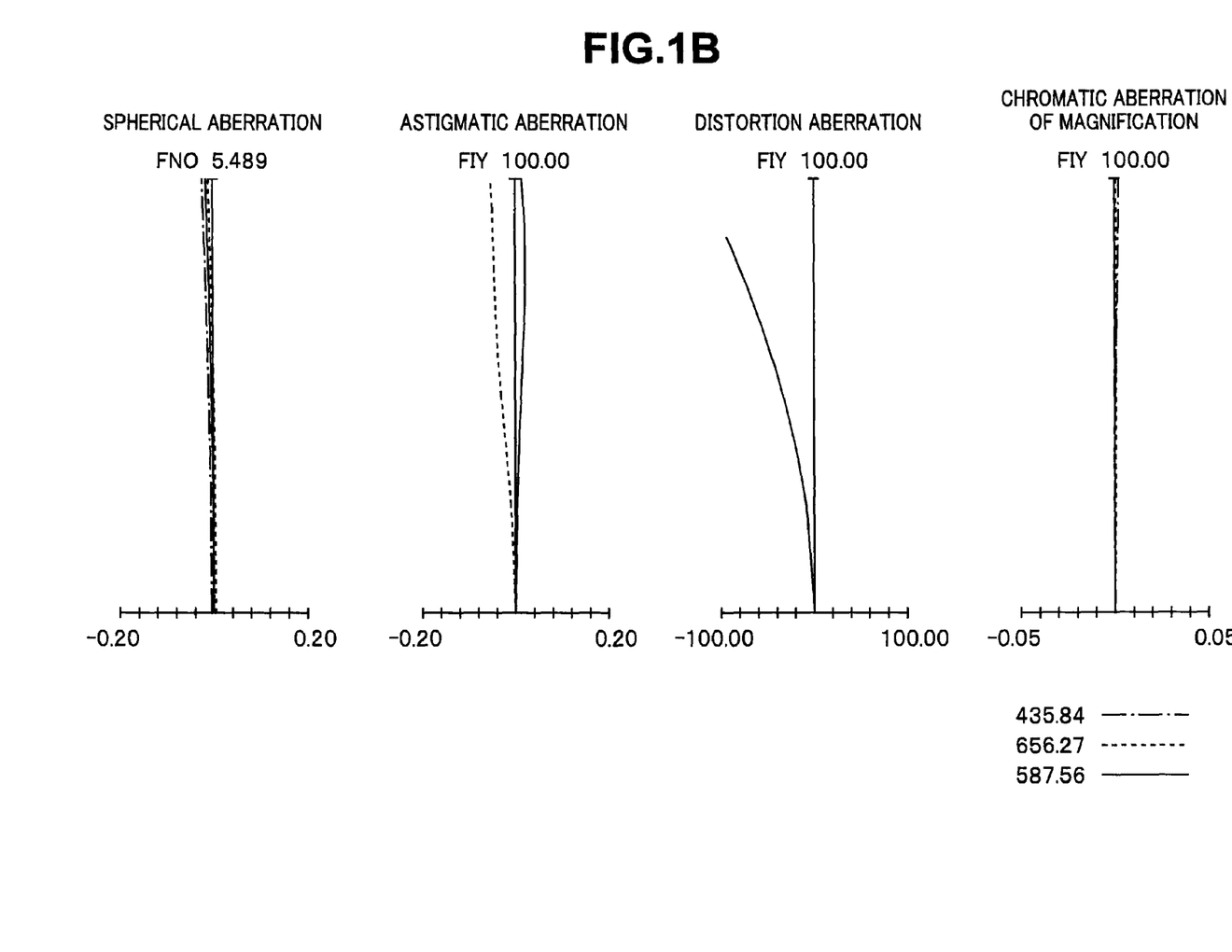
FIG. 1B includes diagrams illustrating a spherical aberration, an astigmatic aberration, a distortion aberration and a chromatic aberration of magnification in the optical system for an endoscope according to the first example of the embodiment.

FIG. 1A is a diagram illustrating a configuration of the optical system for an endoscope according to a first example, along an optical path, and FIG. 1B includes diagrams illustrating a spherical aberration, an astigmatic aberration, a distortion aberration and a chromatic aberration of magnification in the optical system for an endoscope according to the first example.

Here, in each of the spherical aberration diagram and the chromatic aberration of magnification diagram in the aberration diagrams, the alternate long and short dash line indicates a g-line (wavelength: 435.84 nm), the solid line indicates a d-line (wavelength: 587.56 nm) and the dotted line indicates a C-line (wavelength: 656.27 nm), respectively. Also, in the astigmatic aberration diagram in the aberration diagrams, the dotted line indicates a meridional line M and the solid line indicates a sagittal line S, respectively. Note that FIY in the aberration diagrams represents a half field angle and FNO. in the aberration diagrams and the below numeral data represents an F-number.

Numerical data of the optical system according to the first example are indicated below.

| Surface number | Curvature radius | Surface distance | Refractive index | Abbe's number vd |
|---|---|---|---|---|
| 1 | 4.142 | 0.30 | 1.77000 | 73.00 |
| 2 | 0.625 | 0.29 | | |
| 3 | −2.011 | 0.25 | 2.00330 | 28.27 |
| 4 | 1.378 | 0.50 | | |
| 5 | (Diaphragm) | 0.40 | | |
| 6 | −2.094 | 0.50 | 1.88300 | 40.76 |
| 7 | −1.186 | 0.05 | | |
| 8 | ∞ | 0.65 | 1.64769 | 33.79 |
| 9 | −1.721 | 0.05 | | |
| 10 | ∞ | 0.60 | 1.51965 | 75.01 |
| 11 | ∞ | 0.05 | | |
| 12 | 2.478 | 0.88 | 1.72916 | 54.68 |
| 13 | −1.148 | 0.30 | 1.92286 | 18.90 |
| 14 | 1.812 | 0.60 | 1.88300 | 40.76 |
| 15 | −7.685 | 0.25 | | |
| 16 | ∞ | 0.50 | 1.51633 | 64.14 |
| 17 | ∞ | 0.01 | 1.51000 | 63.01 |
| 18 | ∞ | 0.50 | 1.51633 | 64.14 |
| 19 | ∞ | Image surface | | |

| | |
|---|---|
| Focal length | 0.41 |
| FNO. | 5.49 |
| Field angle 2ω | 200.00 |
| Flange focal length (in the air) | 0.90 |
| Total length (in the air) | 6.32 |

Second Example

Figure 2A:
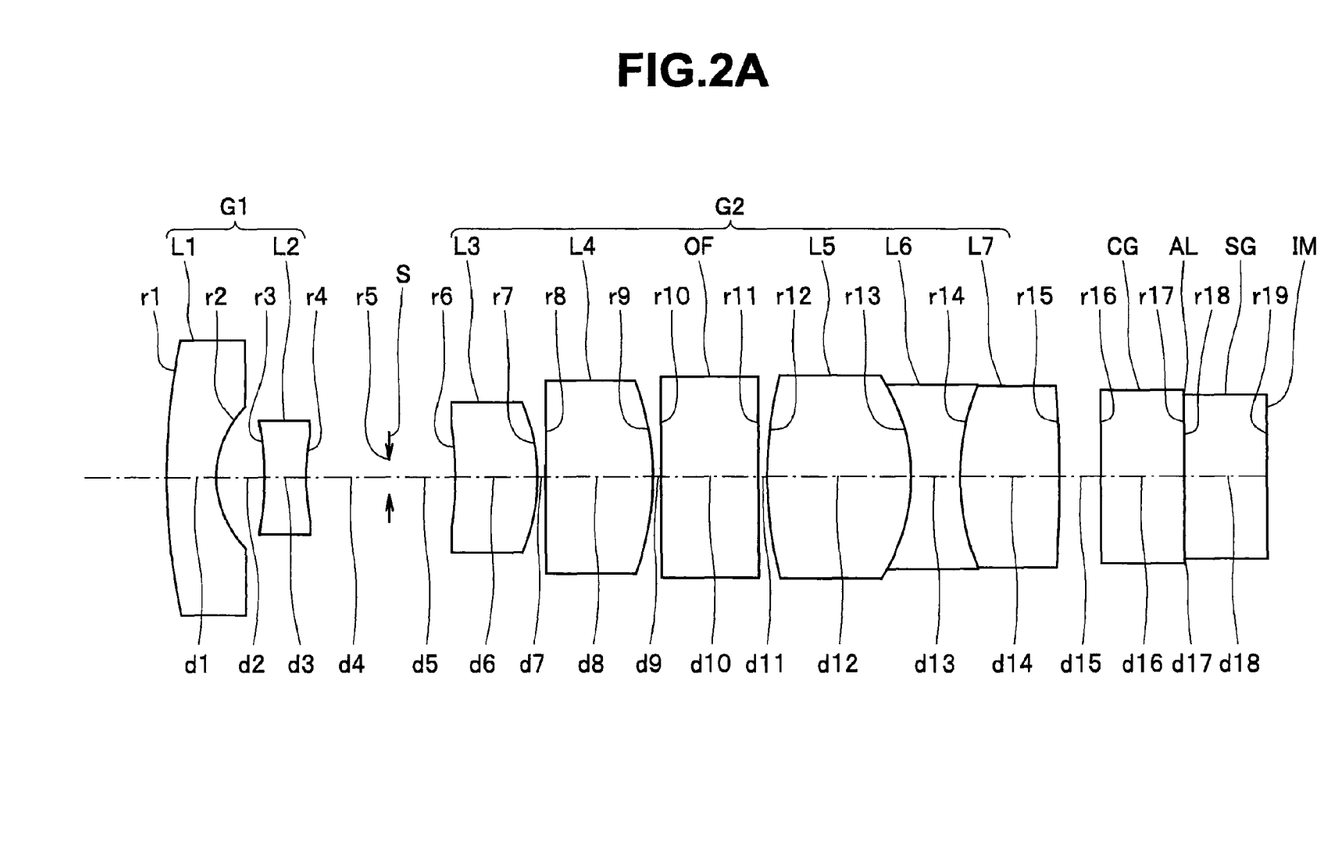
FIG. 2A is a diagram illustrating a configuration of an optical system for an endoscope according to a second example of the embodiment, along an optical path.
Figure 2B:
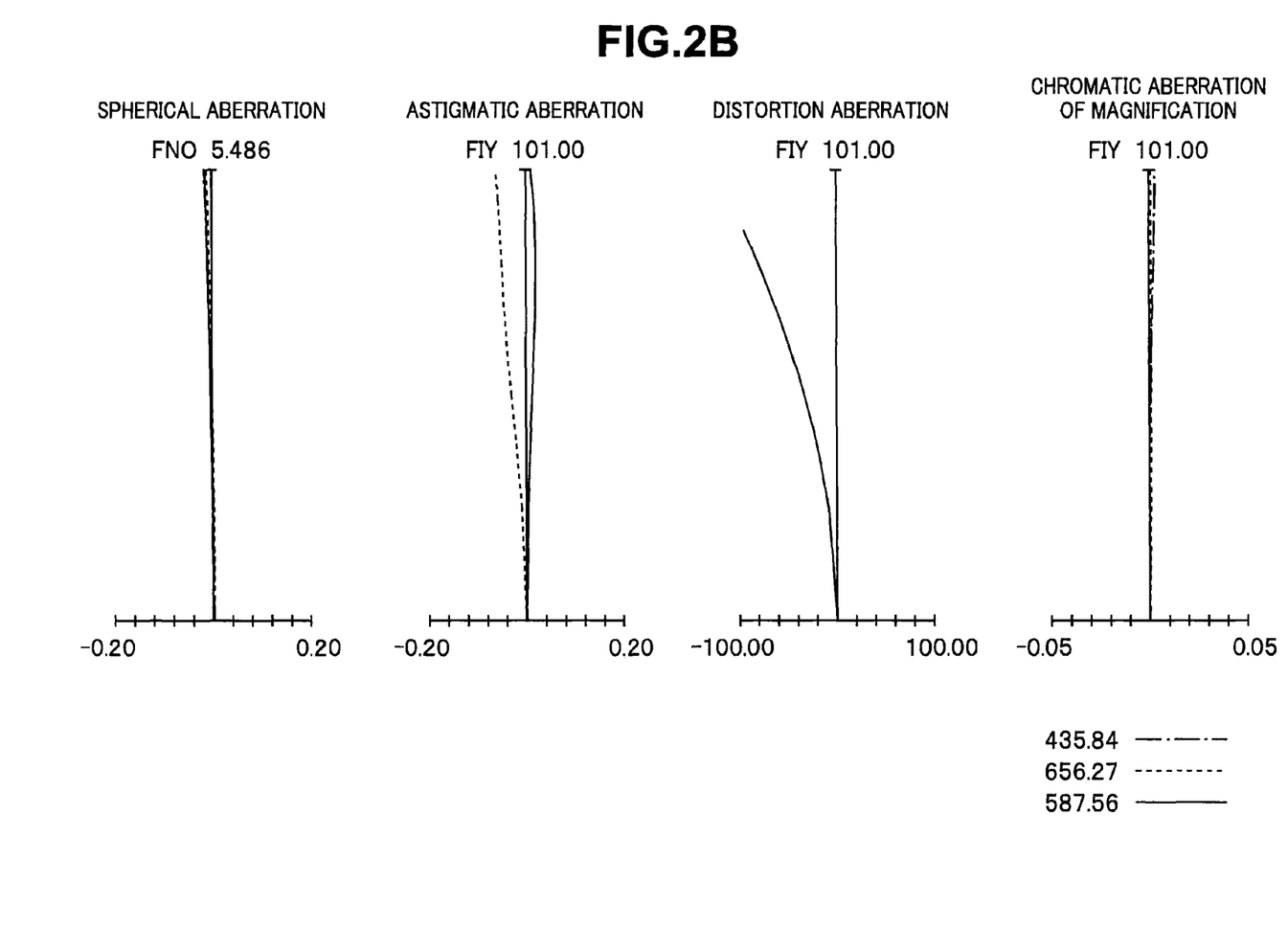
FIG. 2B includes diagrams illustrating a spherical aberration, an astigmatic aberration, a distortion aberration and a chromatic aberration of magnification in the optical system for an endoscope according to the second example of the embodiment.

FIG. 2A is a diagram illustrating a configuration of the optical system for an endoscope according to a second example, along an optical path, and FIG. 2B includes diagrams illustrating a spherical aberration, an astigmatic aberration, a distortion aberration and a chromatic aberration of magnification in the optical system for an endoscope according to the second example.

Here, in each of the spherical aberration diagram and the chromatic aberration of magnification diagram in the aberration diagrams, the alternate long and short dash line indicates a g-line (wavelength: 435.84 nm), the solid line indicates a d-line (wavelength: 587.56 nm) and the dotted line indicates a C-line (wavelength: 656.27 nm), respectively. Also, in the astigmatic aberration diagram in the aberration diagrams, the dotted line indicates a meridional line M and the solid line indicates a sagittal line S, respectively. Note that FIY in the aberration diagrams represents a half field angle and FNO. in the aberration diagrams and the below numeral data represents an F-number.

Numerical data of the optical system according to the second example are indicated below.

| Surface number | Curvature radius | Surface distance | Refractive index | Abbe's number vd |
|---|---|---|---|---|
| 1 | 3.579 | 0.30 | 1.88300 | 40.76 |
| 2 | 0.625 | 0.29 | | |
| 3 | −2.546 | 0.25 | 2.00330 | 28.27 |
| 4 | 1.228 | 0.50 | | |
| 5 | (Diaphragm) | 0.40 | | |
| 6 | −1.960 | 0.50 | 1.88300 | 40.76 |
| 7 | −1.165 | 0.05 | | |
| 8 | ∞ | 0.65 | 1.64769 | 33.79 |
| 9 | −1.706 | 0.05 | | |
| 10 | ∞ | 0.60 | 1.51965 | 75.01 |
| 11 | ∞ | 0.05 | | |
| 12 | 2.391 | 0.88 | 1.72916 | 54.68 |
| 13 | −1.130 | 0.30 | 1.92286 | 18.90 |
| 14 | 1.525 | 0.60 | 1.88300 | 40.76 |
| 15 | −8.156 | 0.25 | | |
| 16 | ∞ | 0.50 | 1.51633 | 64.14 |
| 17 | ∞ | 0.01 | 1.51000 | 63.01 |
| 18 | ∞ | 0.50 | 1.51633 | 64.14 |
| 19 | ∞ | Image surface | | |

| | |
|---|---|
| Focal length | 0.40 |
| FNO. | 5.49 |
| Field angle 2ω | 202.00 |
| Flange focal length (in the air) | 0.89 |
| Total length (in the air) | 6.31 |

Third Example

Figure 3A:
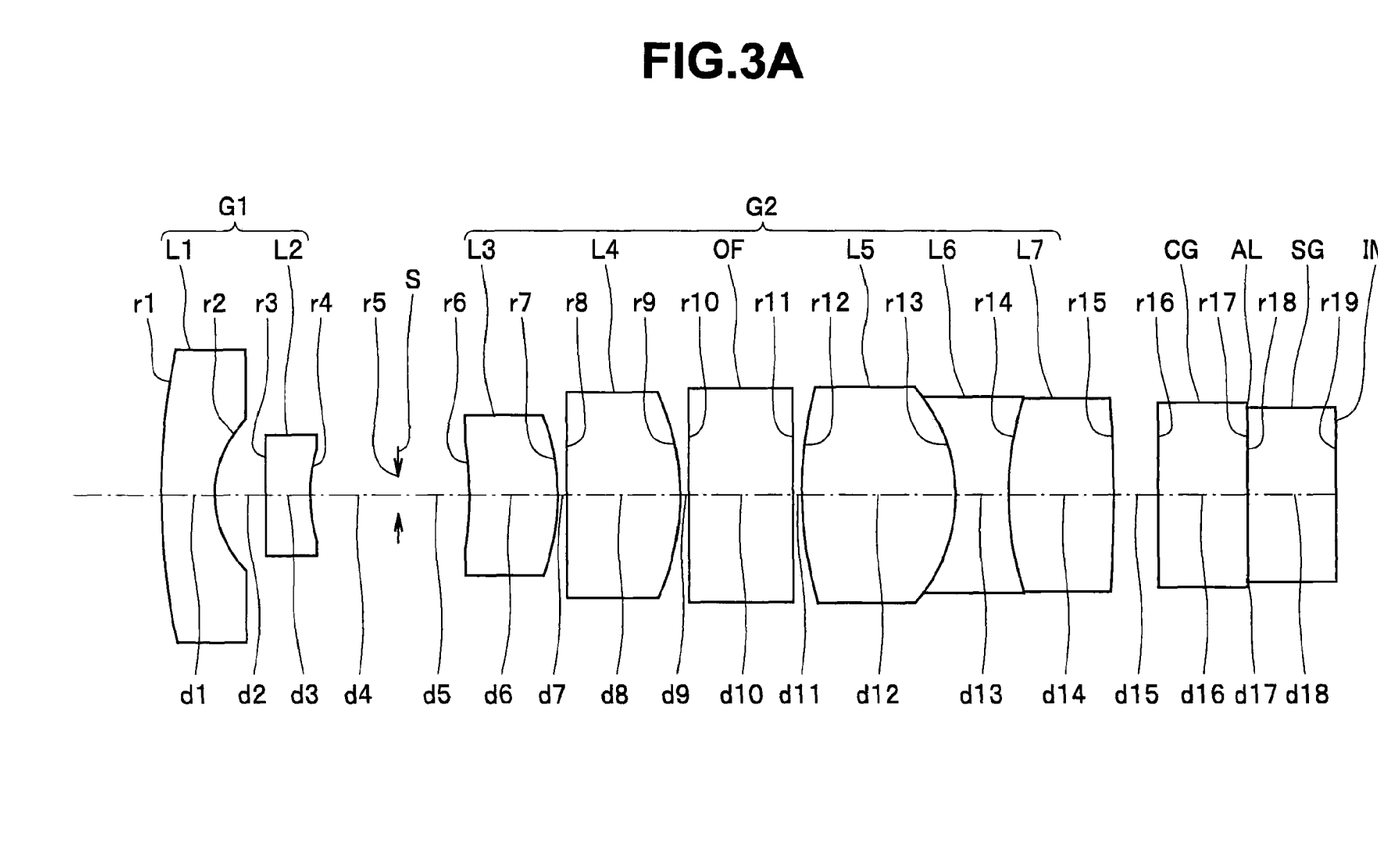
FIG. 3A is a diagram illustrating a configuration of an optical system for an endoscope according to a third example of the embodiment, along an optical path.
Figure 3B:
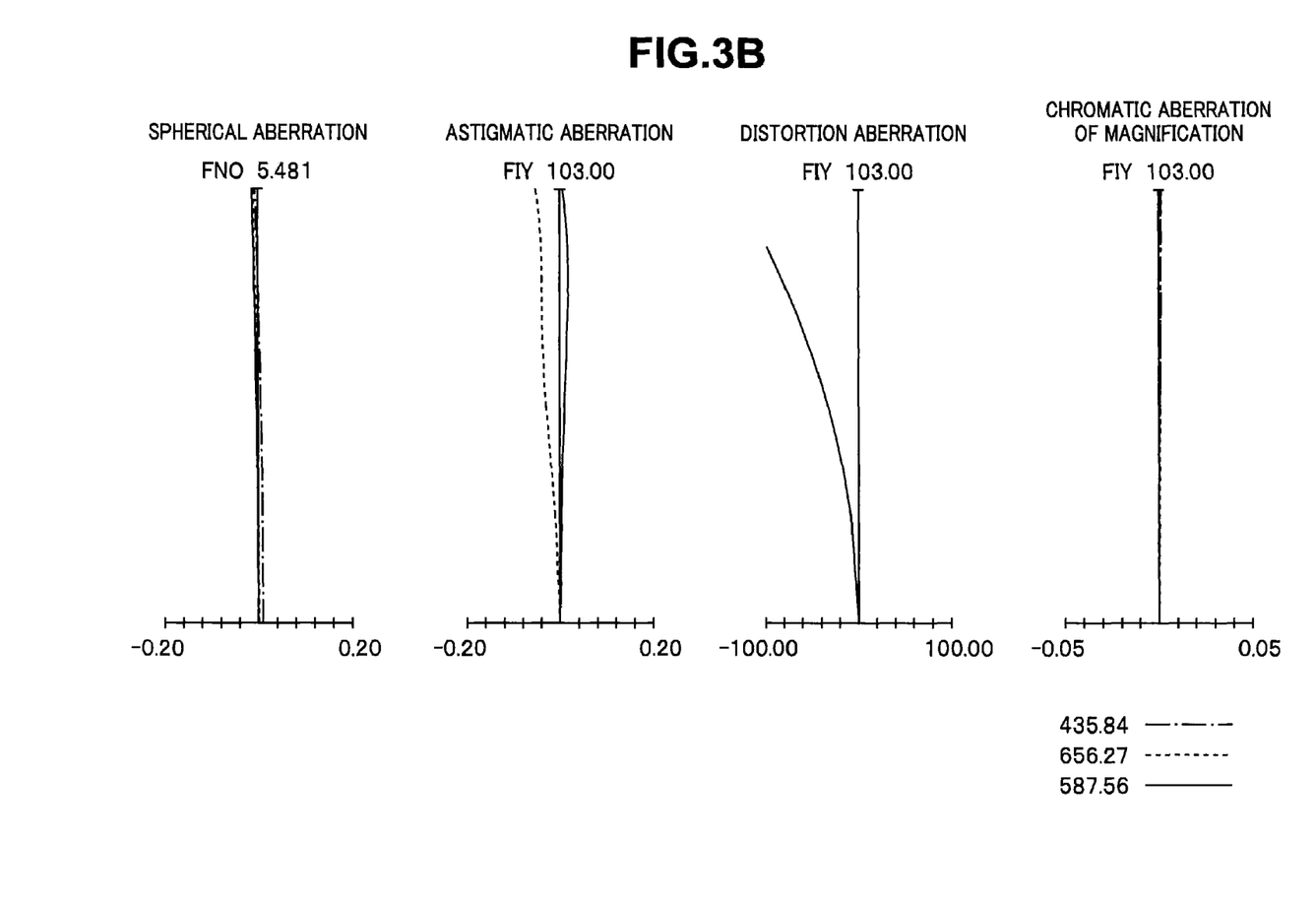
FIG. 3B includes diagrams illustrating a spherical aberration, an astigmatic aberration, a distortion aberration and a chromatic aberration of magnification in the optical system for an endoscope according to the third example of the embodiment.

FIG. 3A is a diagram illustrating a configuration of the optical system for an endoscope according to a third example, along an optical path, and FIG. 3B includes diagrams illustrating a spherical aberration, an astigmatic aberration, a distortion aberration and a chromatic aberration of magnification in the optical system for an endoscope according to the third example.

Here, in each of the spherical aberration diagram and the chromatic aberration of magnification diagram in the aberration diagrams, the alternate long and short dash line indicates a g-line (wavelength: 435.84 nm), the solid line indicates a d-line (wavelength: 587.56 nm) and the dotted line indicates a C-line (wavelength: 656.27 nm), respectively. Also, in the astigmatic aberration diagram in the aberration diagrams, the dotted line indicates a meridional line M and the solid line indicates a sagittal line S, respectively. Note that FIY in the aberration diagrams represents a half field angle and FNO. in the aberration diagrams and the below numeral data represents an F-number.

Numerical data of the optical system according to the third example are indicated below.

| Surface number | Curvature radius | Surface distance | Refractive index | Abbe's number vd |
|---|---|---|---|---|
| 1 | 2.891 | 0.30 | 2.17000 | 33.00 |
| 2 | 0.625 | 0.29 | | |
| 3 | −84.848 | 0.25 | 2.00330 | 28.27 |
| 4 | 0.860 | 0.50 | | |
| 5 | (Diaphragm) | 0.40 | | |
| 6 | −2.264 | 0.50 | 1.88300 | 40.76 |
| 7 | −1.347 | 0.05 | | |
| 8 | ∞ | 0.65 | 1.64769 | 33.79 |
| 9 | −1.484 | 0.05 | | |
| 10 | ∞ | 0.60 | 1.51965 | 75.01 |
| 11 | ∞ | 0.05 | | |
| 12 | 2.157 | 0.88 | 1.72916 | 54.68 |
| 13 | −0.948 | 0.30 | 1.92286 | 18.90 |
| 14 | 1.702 | 0.60 | 1.88300 | 40.76 |
| 15 | −9.072 | 0.25 | | |
| 16 | ∞ | 0.50 | 1.51633 | 64.14 |
| 17 | ∞ | 0.01 | 1.51000 | 63.01 |
| 18 | ∞ | 0.50 | 1.51633 | 64.14 |
| 19 | ∞ | Image surface | | |

| | |
|---|---|
| Focal length | 0.36 |
| FNO. | 5.49 |
| Field angle 2ω | 206.00 |
| Flange focal length (in the air) | 0.89 |
| Total length (in the air) | 6.31 |

Fourth Example

Figure 4A:
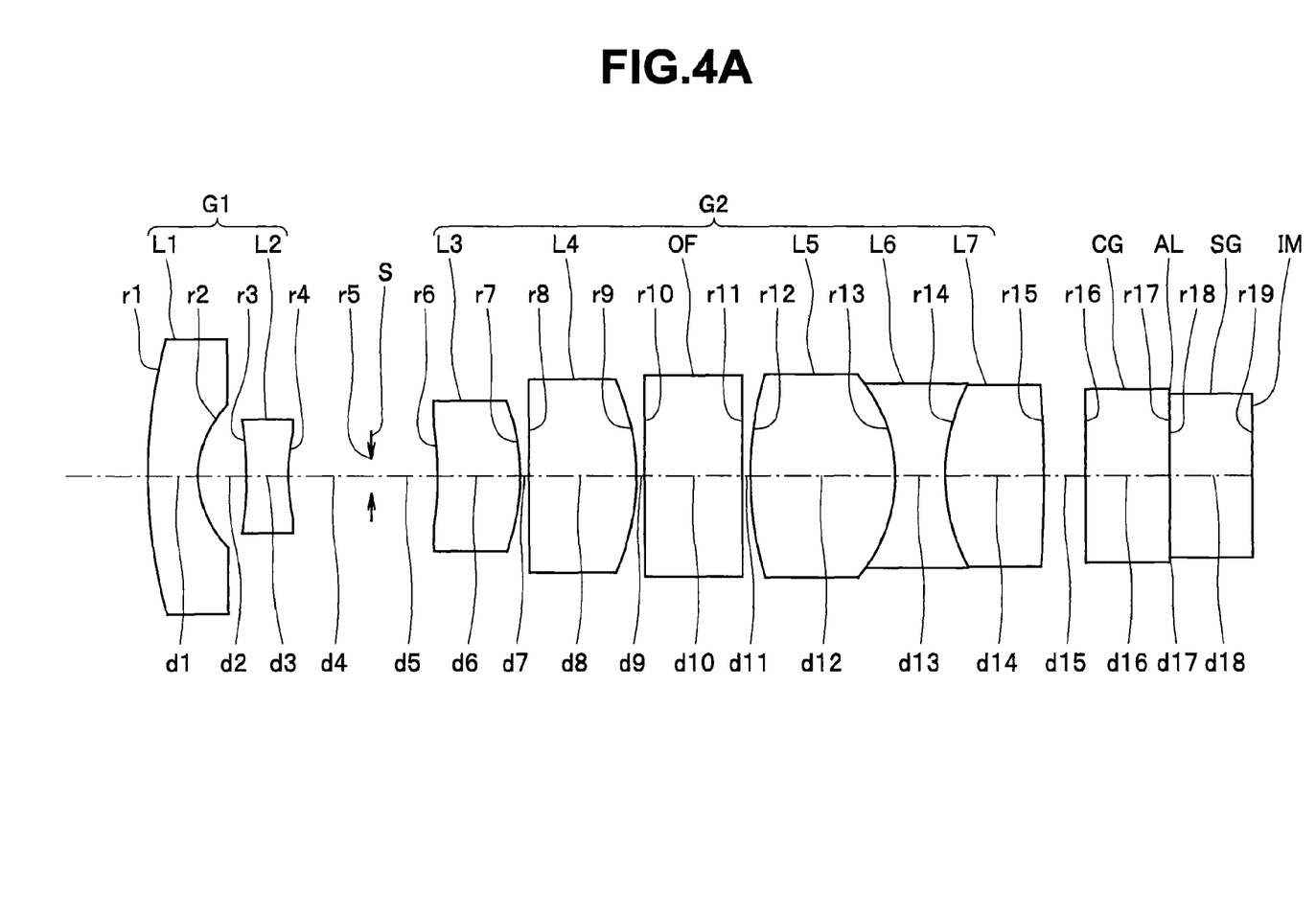
FIG. 4A is a diagram illustrating a configuration of an optical system for an endoscope according to a fourth example of the embodiment, along an optical path.
Figure 4B:
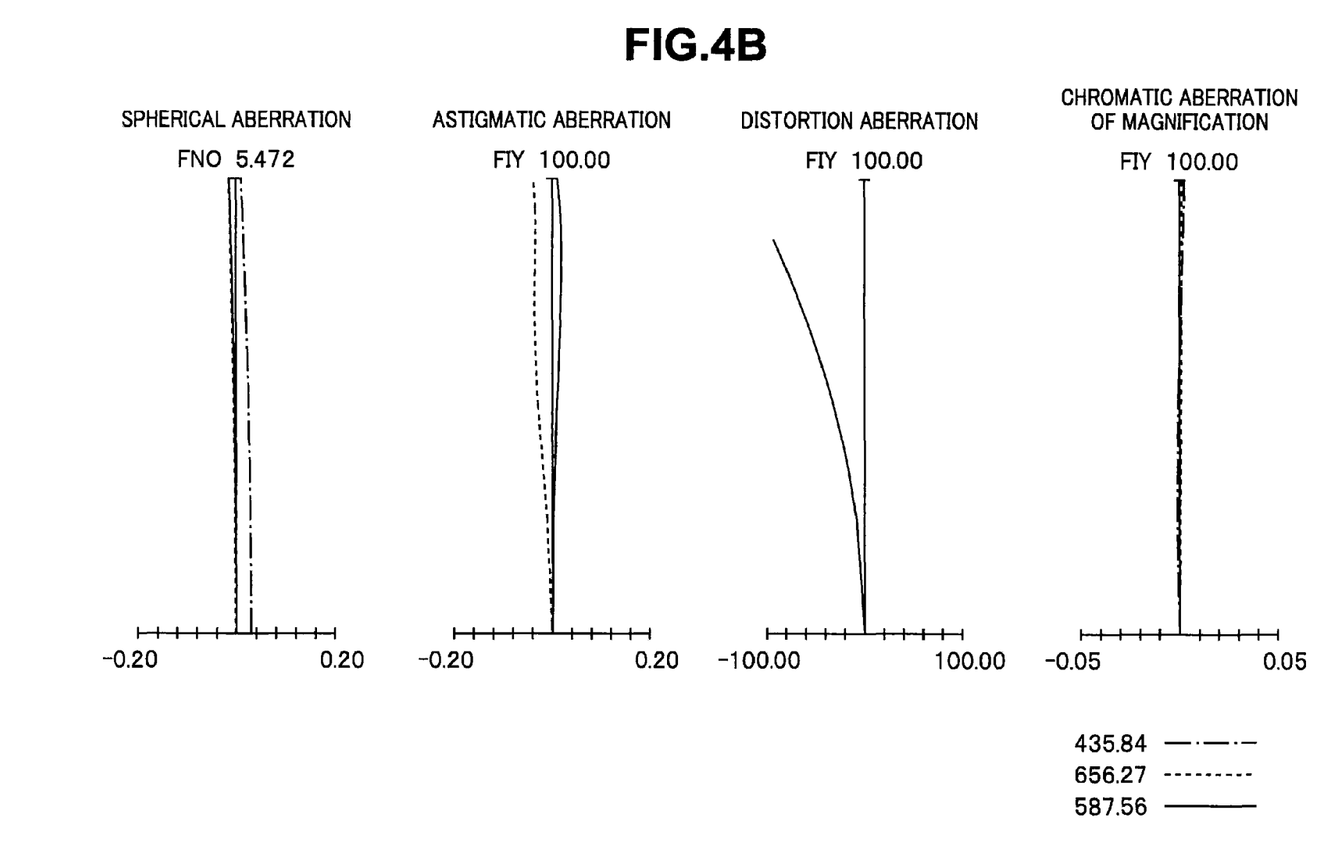
FIG. 4B includes diagrams illustrating a spherical aberration, an astigmatic aberration, a distortion aberration and a chromatic aberration of magnification in the optical system for an endoscope according to the fourth example of the embodiment.

FIG. 4A is a diagram illustrating a configuration of the optical system for an endoscope according to a fourth example, along an optical path, and FIG. 4B includes diagrams illustrating a spherical aberration, an astigmatic aberration, a distortion aberration and a chromatic aberration of magnification in the optical system for an endoscope according to the fourth example.

Here, in each of the spherical aberration diagram and the chromatic aberration of magnification diagram in the aberration diagrams, the alternate long and short dash line indicates a g-line (wavelength: 435.84 nm), the solid line indicates a d-line (wavelength: 587.56 nm) and the dotted line indicates a C-line (wavelength: 656.27 nm), respectively. Also, in the astigmatic aberration diagram in the aberration diagrams, the dotted line indicates a meridional line M and the solid line indicates a sagittal line S, respectively. Note that FIY in the aberration diagrams represents a half field angle and FNO. in the aberration diagrams and the below numeral data represents an F-number.

Numerical data of the optical system according to the fourth example are indicated below.

| Surface number | Curvature radius | Surface distance | Refractive index | Abbe's number vd |
|---|---|---|---|---|
| 1 | 3.149 | 0.30 | 2.00178 | 19.32 |
| 2 | 0.625 | 0.29 | | |
| 3 | −3.207 | 0.25 | 2.00330 | 28.27 |
| 4 | 1.159 | 0.50 | | |
| 5 | (Diaphragm) | 0.40 | | |
| 6 | −2.190 | 0.50 | 1.88300 | 40.76 |
| 7 | −1.346 | 0.05 | | |
| 8 | ∞ | 0.65 | 1.64769 | 33.79 |
| 9 | −1.484 | 0.05 | | |
| 10 | ∞ | 0.60 | 1.51965 | 75.01 |
| 11 | ∞ | 0.05 | | |
| 12 | 2.179 | 0.88 | 1.72916 | 54.68 |
| 13 | −0.966 | 0.30 | 1.92286 | 18.90 |
| 14 | 1.182 | 0.60 | 1.88300 | 40.76 |
| 15 | −7.929 | 0.25 | | |
| 16 | ∞ | 0.50 | 1.51633 | 64.14 |
| 17 | ∞ | 0.01 | 1.51000 | 63.01 |
| 18 | ∞ | 0.50 | 1.51633 | 64.14 |
| 19 | ∞ | Image surface | | |

-continued

| | |
|---|---|
| Focal length | 0.38 |
| FNO. | 5.47 |
| Field angle 2ω | 200.00 |
| Flange focal length (in the air) | 0.89 |
| Total length (in the air) | 6.31 |

Fifth Example

Figure 5A:
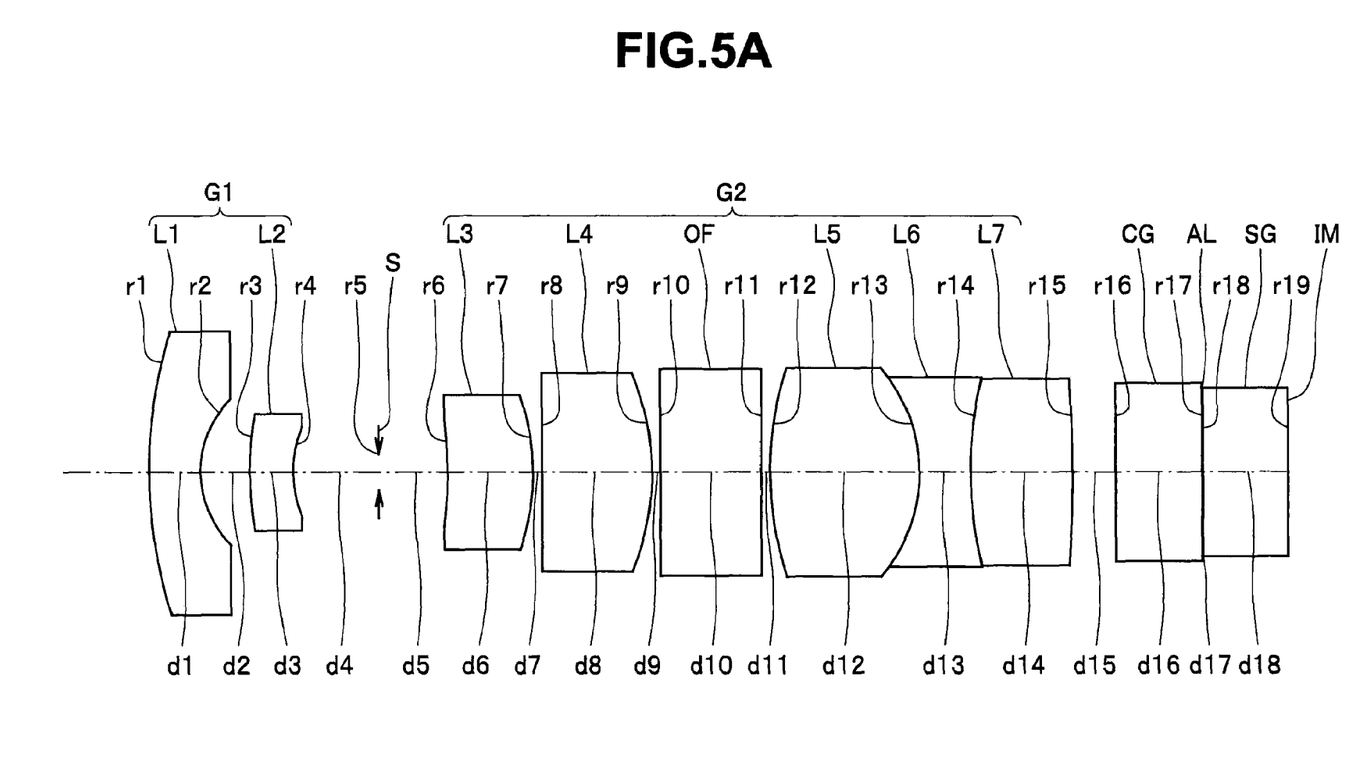
FIG. 5A is a diagram illustrating a configuration of an optical system for an endoscope according to a fifth example of the embodiment, along an optical path.
Figure 5B:
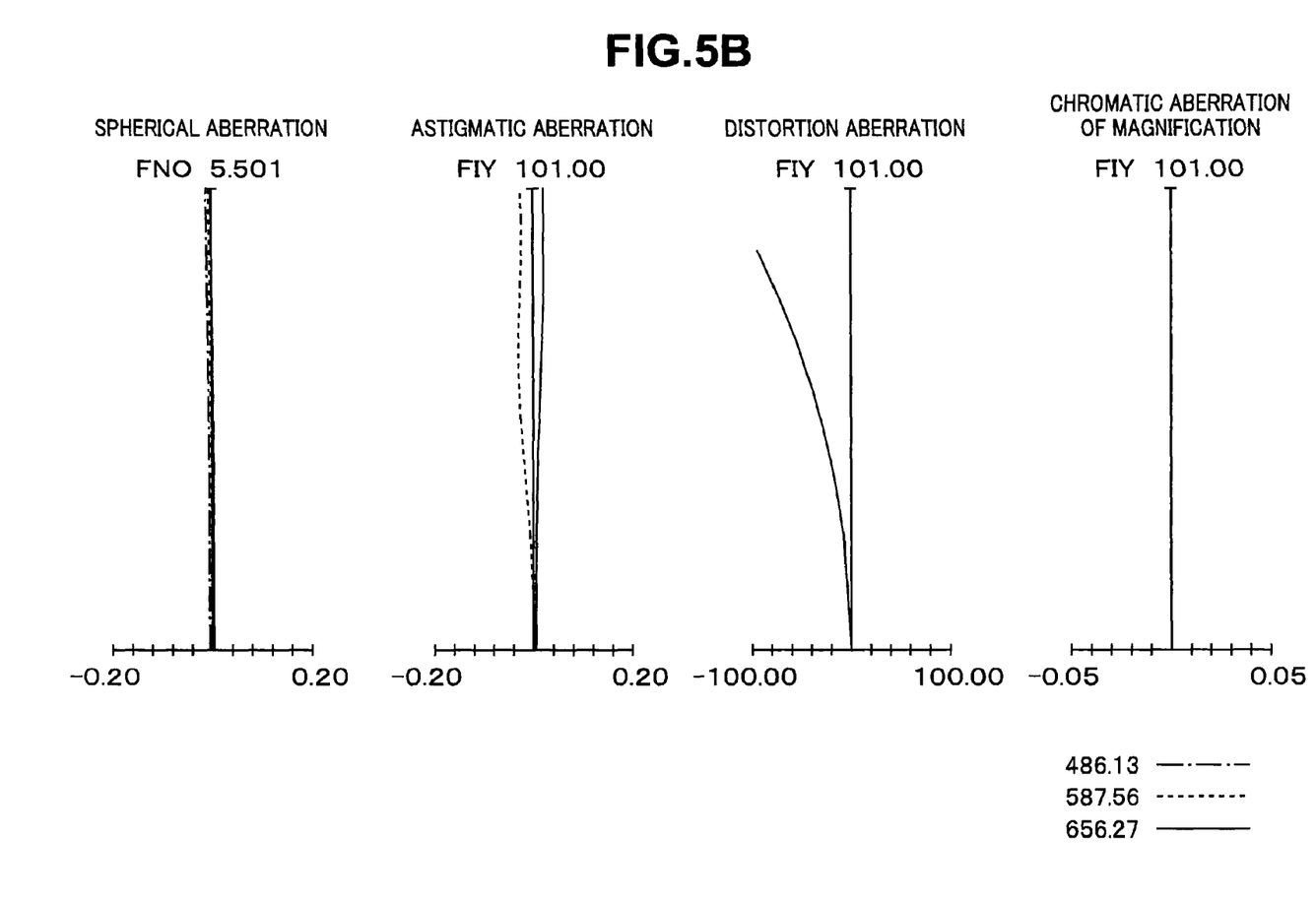
FIG. 5B includes diagrams illustrating a spherical aberration, an astigmatic aberration, a distortion aberration and a chromatic aberration of magnification in the optical system for an endoscope according to the fifth example of the embodiment.

FIG. 5A is a diagram illustrating a configuration of the optical system for an endoscope according to a fifth example, along an optical path, and FIG. 5B includes diagrams illustrating a spherical aberration, an astigmatic aberration, a distortion aberration and a chromatic aberration of magnification in the optical system for an endoscope according to the fifth example.

Here, in each of the spherical aberration diagram and the chromatic aberration of magnification diagram in the aberration diagrams, the alternate long and short dash line indicates an F-line (wavelength: 486.13 nm), the dotted line indicates a d-line (wavelength: 587.56 nm) and the solid line indicates a C-line (wavelength: 656.27 nm), respectively. Also, in the astigmatic aberration diagram in the aberration diagrams, the dotted line indicates a meridional line M and the solid line indicates a sagittal line S, respectively. Note that FIY in the aberration diagrams represents a half field angle and FNO. in the aberration diagrams and the below numeral data represents an F-number.

Numerical data of the optical system according to the fifth example are indicated below.

| Surface number | Curvature radius | Surface distance | Refractive index | Abbe's number vd |
|---|---|---|---|---|
| 1 | 2.637 | 0.30 | 2.42000 | 58.00 |
| 2 | 0.625 | 0.29 | | |
| 3 | 2.034 | 0.25 | 2.00330 | 28.27 |
| 4 | 0.613 | 0.50 | | |
| 5 | (Diaphragm) | 0.40 | | |
| 6 | −2.877 | 0.50 | 1.88300 | 40.76 |
| 7 | −1.438 | 0.05 | | |
| 8 | ∞ | 0.65 | 1.64769 | 33.79 |
| 9 | −1.547 | 0.05 | | |
| 10 | ∞ | 0.60 | 1.51965 | 75.01 |
| 11 | ∞ | 0.05 | | |
| 12 | 1.994 | 0.88 | 1.72916 | 54.68 |
| 13 | −0.973 | 0.30 | 1.92286 | 18.90 |
| 14 | 2.346 | 0.60 | 1.88300 | 40.76 |
| 15 | −14.176 | 0.25 | | |
| 16 | ∞ | 0.50 | 1.51633 | 64.14 |
| 17 | ∞ | 0.01 | 1.51000 | 63.01 |
| 18 | ∞ | 0.50 | 1.51633 | 64.14 |
| 19 | ∞ | Image surface | | |

| | |
|---|---|
| Focal length | 0.35 |
| FNO. | 5.50 |
| Field angle 2ω | 202.00 |
| Flange focal length (in the air) | 0.89 |
| Total length (in the air) | 6.31 |

Sixth Example

Figure 6A:
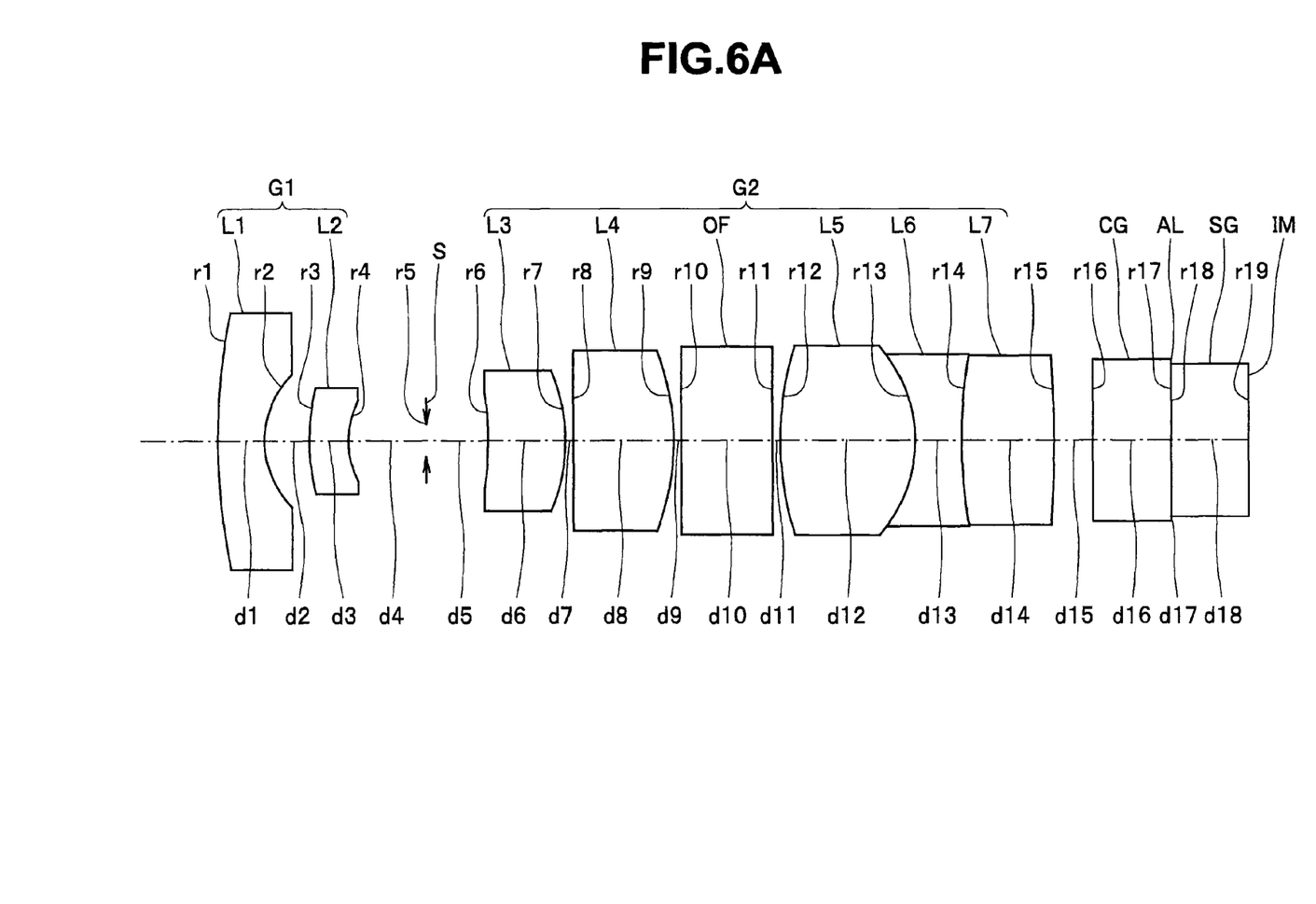
FIG. 6A is a diagram illustrating a configuration of an optical system for an endoscope according to a sixth example of the embodiment, along an optical path.
Figure 6B:
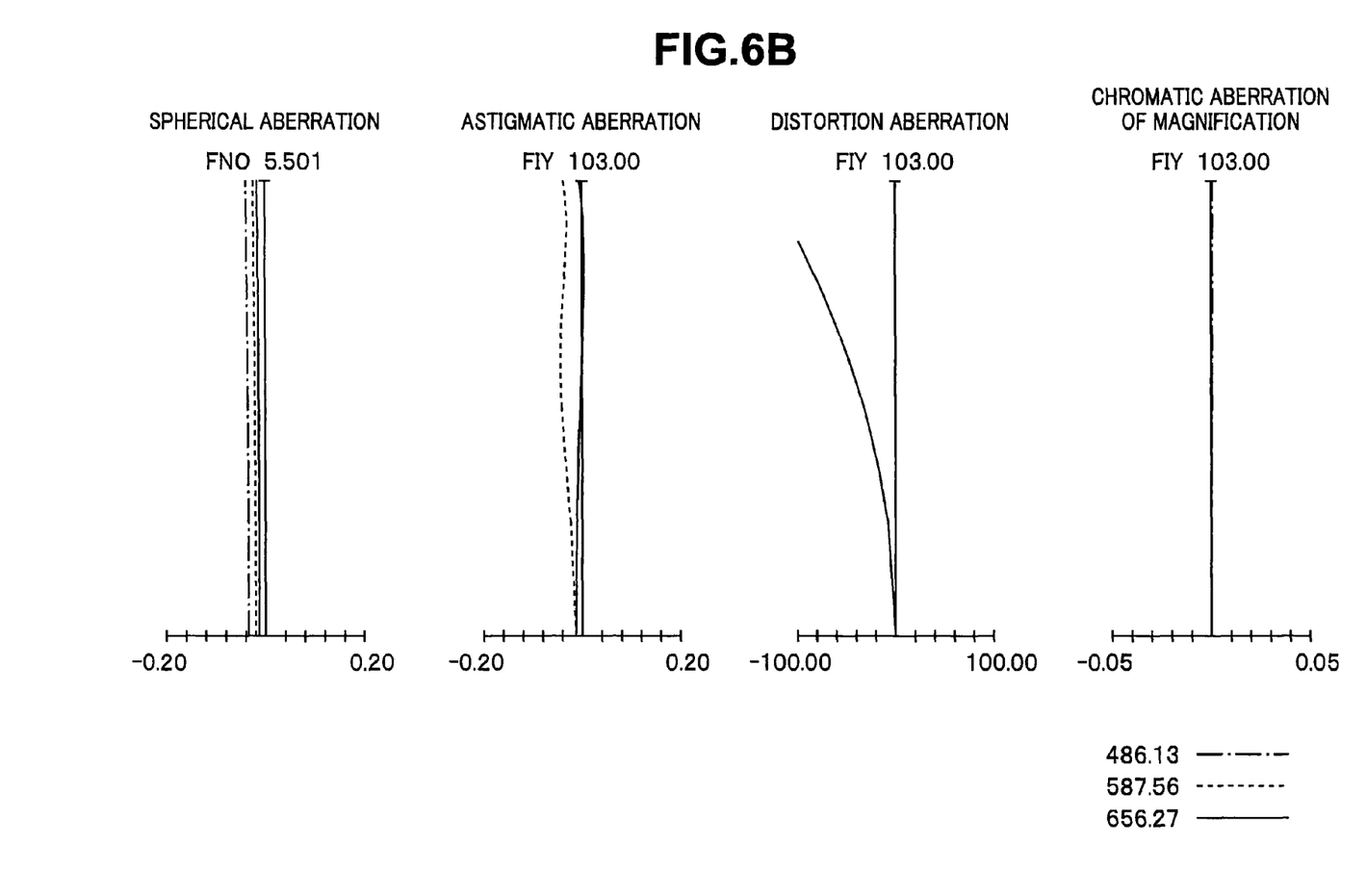
FIG. 6B includes diagrams illustrating a spherical aberration, an astigmatic aberration, a distortion aberration and a chromatic aberration of magnification in the optical system for an endoscope according to the sixth example of the embodiment.

FIG. 6A is a diagram illustrating a configuration of the optical system for an endoscope according to a sixth example, along an optical path, and FIG. 6B includes diagrams illustrating a spherical aberration, an astigmatic aberration, a distortion aberration and a chromatic aberration of magnification in the optical system for an endoscope according to the sixth example.

Here, in each of the spherical aberration diagram and the chromatic aberration of magnification diagram in the aberration diagrams, the alternate long and short dash line indicates an F-line (wavelength: 486.13 nm), the dotted line indicates a d-line (wavelength: 587.56 nm) and the solid line indicates a C-line (wavelength: 656.27 nm), respectively. Also, in the astigmatic aberration diagram in the aberration diagrams, the dotted line indicates a meridional line M and the solid line indicates a sagittal line S, respectively. Note that FIY in the aberration diagrams represents a half field angle and FNO. in the aberration diagrams and the below numeral data represents an F-number.

Numerical data of the optical system according to the sixth example are indicated below.

| Surface number | Curvature radius | Surface distance | Refractive index | Abbe's number vd |
|---|---|---|---|---|
| 1 | 2.811 | 0.30 | 2.42000 | 58.00 |
| 2 | 0.700 | 0.29 | | |
| 3 | 1.415 | 0.25 | 2.42000 | 58.00 |
| 4 | 0.544 | 0.50 | | |
| 5 | (Diaphragm) | 0.40 | | |
| 6 | −3.332 | 0.50 | 1.88300 | 40.76 |
| 7 | −1.329 | 0.05 | | |
| 8 | ∞ | 0.65 | 1.64769 | 33.79 |
| 9 | −1.698 | 0.05 | | |
| 10 | ∞ | 0.60 | 1.51965 | 75.01 |
| 11 | ∞ | 0.05 | | |
| 12 | 2.059 | 0.88 | 1.72916 | 54.68 |
| 13 | −0.948 | 0.30 | 1.92286 | 18.90 |
| 14 | 3.307 | 0.60 | 1.88300 | 40.76 |
| 15 | −10.876 | 0.25 | | |
| 16 | ∞ | 0.50 | 1.51633 | 64.14 |
| 17 | ∞ | 0.01 | 1.51000 | 63.01 |
| 18 | ∞ | 0.50 | 1.51633 | 64.14 |
| 19 | ∞ | Image surface | | |

| | |
|---|---|
| Focal length | 0.36 |
| FNO. | 5.50 |
| Field angle 2ω | 206.00 |
| Flange focal length (in the air) | 0.89 |
| Total length (in the air) | 6.31 |

According to such embodiment, in an optical system for an endoscope having a field angle of no less than 200 degrees, a distance from a negative first lens to an aperture diaphragm is reduced to move a position of an entrance pupil to the object side, enabling reduction in diameter of the negative first lens. Furthermore, an amount of refraction of a surface on the object side of the negative first lens is properly determined for an incident angle that corresponds to a half field angle of 100 degrees, enabling occurrence of various aberrations to be favorably suppressed.

Consequently, a small-diameter optical system for an endoscope that is suitable for use in an endoscope (for example, a urological endoscope or any of other endoscopes) can be provided.

Note that the present invention is not limited to the above-described embodiment as it is, and in the practical phase, the present invention can be embodied with components modified without departing from the spirit of the present invention. Furthermore, various aspects of the invention can be provided by arbitrary combinations of a plurality of components disclosed in the above-described embodiment. For example, several components may be deleted from all the components indicated in the embodiment. Furthermore, components may arbitrarily be combined through the different embodiments. As described above, it should be understood that various modifications and applications are possible without departing from the spirit of the invention.

What is claimed is:

1. An optical system for an endoscope, the optical system comprising:

a negative lens group, an aperture diaphragm and a positive lens group in this order from an object side, wherein the negative lens group includes a negative first lens and a negative second lens in this order from the object side; and wherein the optical system meets conditional expressions (1) and (2):

$$0.05 < H(100) \times (nd01-1)/Rf01 < 0.38 \quad (1)$$

and $$0.5 < enp/FL < 2.5 \quad (2),$$

where:

$H(100)$ is a height at which a principal ray with a field angle of incidence of 100 degrees falls on a surface on the object side of the first lens;

$Rf01$ is a curvature radius of the surface on the object side of the first lens;

$nd01$ is a refractive index of the first lens;

FL is a focal length of an entire system; and enp is a distance between an entrance pupil and the surface on the object side of the first lens.

2. The optical system for an endoscope according to claim 1, wherein the optical system further meets conditional expressions (3) and (4):

$$0.5 < H(100)/FL < 3.5 \quad (3);$$

and $$1.1 < (r1+r2)/(r1-r2) < 1.9 \quad (4),$$

where:

r1 is the curvature radius of the surface on the object side of the first lens; and r2 is a curvature radius of a surface on an image side of the first lens.

3. The optical system for an endoscope according to claim 1, wherein where a lens system incident angle ω=100, the optical system further meets conditional expression (5):

$$0.00 < |EX(\omega)|/\omega < 0.03 \quad (5),$$

where $EX(\omega)$ is an angle at which a principal ray incident at the incident angle co exits from the optical system.

4. The optical system for an endoscope according to claim 1, wherein the optical system further meets conditional expression (6):

$$-8.0 < F\_front/F\_rear < -0.1 \quad (6),$$

where F_front is a focal length of the negative lens group and F_rear is a focal length of the positive lens group.

5. The optical system for an endoscope according to claim 1, wherein the optical system further meets conditional expressions (7) and (8):

$$1.77 < nd1 < 2.42 \quad (7);$$

and $$1.9 < nd2 < 2.42 \quad (8),$$

where nd1 is the refractive index of the negative first lens and nd2 is a refractive index of the negative second lens.

6. The optical system for an endoscope according to claim 1, wherein the positive lens group includes at least one positive lens and a joined lens including a positive lens and a negative lens, in this order from the object side.

7. The optical system for an endoscope according to claim 1, wherein the optical system further meets conditional expression (9):

$$0.1 < PW\_1/PW\_2 < 0.26 \quad (9),$$

where PW_1 is a power of the negative first lens and PW_2 is a power of the negative second lens.

8. The optical system for an endoscope according to claim 1, wherein all of optical elements having a power in the optical system for an endoscope are spherical lenses.

* * * * *